United States Patent
Liu et al.

(10) Patent No.: US 12,087,482 B2
(45) Date of Patent: Sep. 10, 2024

(54) FLEXIBLE PERMANENT MAGNETIC MATERIAL, PREPARATION METHOD AND APPLICATION THEREOF IN MAGNETIC BIOLOGICAL EFFECT PRODUCTS

(71) Applicant: PEKING UNIVERSITY, Beijing (CN)

(72) Inventors: Shunquan Liu, Beijing (CN); Jinbo Yang, Beijing (CN); Jingzhi Han, Beijing (CN); Yu He, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 0 days.

(21) Appl. No.: 18/458,975

(22) Filed: Aug. 30, 2023

(65) Prior Publication Data

US 2024/0096530 A1  Mar. 21, 2024

(30) Foreign Application Priority Data

Sep. 20, 2022  (CN) .......................... 202211141192.9

(51) Int. Cl.
| | |
|---|---|
| H01F 1/057 | (2006.01) |
| B22F 1/105 | (2022.01) |
| B22F 3/00 | (2021.01) |
| B22F 3/087 | (2006.01) |
| H01F 1/08 | (2006.01) |
| H01F 7/02 | (2006.01) |

(Continued)

(52) U.S. Cl.
CPC ............ *H01F 1/0578* (2013.01); *B22F 3/004* (2013.01); *B22F 3/087* (2013.01); *H01F 1/083* (2013.01); *H01F 41/00* (2013.01); *A61N 2/06* (2013.01); *B22F 1/105* (2022.01); *B22F 2202/05* (2013.01); *B22F 2301/355* (2013.01); *B22F 2302/256* (2013.01); *B22F 2998/10* (2013.01); *H01F 7/0215* (2013.01)

(58) Field of Classification Search
CPC ..... H01F 1/0578; H01F 7/0215; C03B 20/00; C04B 35/14; C04B 2235/3418
See application file for complete search history.

(56) References Cited

U.S. PATENT DOCUMENTS 3,191,106 A * 6/1965 Baermann ............... H01F 1/117
74/502.5
5,051,200 A   9/1991 Srail
(Continued)

FOREIGN PATENT DOCUMENTS

CN   103745798         4/2014
CN   107301916 A    * 10/2017
(Continued)

OTHER PUBLICATIONS

CN109401640A English language translation (Year: 2019).*
(Continued)

*Primary Examiner* — Samir Shah
*Assistant Examiner* — Sean P. O'Keefe (57) ABSTRACT

A flexible permanent magnetic material, a preparation method and an application thereof in magnetic biological effect products are provides, relating to the technical field of medical equipment. Raw materials of the flexible permanent magnetic material of the application include the following components in parts by weight: 0-70 parts of anisotropic neodymium iron boron powder and 0-40 parts of anisotropic samarium iron nitrogen powder and 3-20 parts of binder.

3 Claims, 8 Drawing Sheets

(51) Int. Cl.
*H01F 41/00* (2006.01)
*A61N 2/06* (2006.01)

(56) References Cited

U.S. PATENT DOCUMENTS

| | | | |
|---|---|---|---|
| 6,387,294 B1 | 5/2002 | Yamashita | |
| 2004/0220445 A1 | 11/2004 | Bove | |
| 2016/0133366 A1* | 5/2016 | Kasamoto | C08J 3/24 156/245 |
| 2019/0348219 A1* | 11/2019 | Hozumi | B22F 1/00 |

FOREIGN PATENT DOCUMENTS

| | | | | |
|---|---|---|---|---|
| CN | 109133716 A * | 1/2019 | | |
| CN | 109401640 | 3/2019 | | |
| CN | 110591262 | 12/2019 | | |
| CN | 111991700 A * | 11/2020 | | |
| CN | 109327770 B * | 12/2020 | | H04R 31/003 |
| CN | 112194903 A * | 1/2021 | | C08L 83/04 |
| CN | 112972779 A * | 6/2021 | | A61L 31/028 |
| CN | 113380484 | 9/2021 | | |
| EP | 1093133 | 4/2001 | | |
| JP | 4265056 B2 * | 5/2009 | | H01F 1/0558 |
| WO | 9850460 | 11/1998 | | |
| WO | 9945998 | 9/1999 | | |

OTHER PUBLICATIONS

CN113380484A English language translation (Year: 2021).*
Chen Hai-Ying, et. al., Magnetostrictions and Magnetic Properties of Nd—Fe—B and $SrFe_{12}O_{19}$, Chin. Phys. Lett. vol. 28, No. 7 (2011) 077501 (4 pages).
Notice of first Office action from SIPO in CN 202211141192.9 dated Jan. 18, 2023, with search report.
Notice of second Office action from SIPO in CN 202211141192.9 dated Mar. 1, 2023, with search report.
Notice of grant patent right for invention from SIPO in CN 202211141192.9 dated Apr. 27, 2023.

* cited by examiner

Lianquan acupoint

FLEXIBLE PERMANENT MAGNETIC MATERIAL, PREPARATION METHOD AND APPLICATION THEREOF IN MAGNETIC BIOLOGICAL EFFECT PRODUCTS

CROSS-REFERENCE TO RELATED APPLICATIONS

This application claims priority of Chinese Patent Application No. 202211141192.9, filed on Sep. 20, 2022, the entire contents of which are incorporated herein by reference.

TECHNICAL FIELD

The application relates to the technical field of medical equipment, and in particular to a flexible permanent magnetic material, a preparation method and an application thereof in magnetic biological effect products.

BACKGROUND

It has been confirmed in many clinical trials that the magnetic field has remarkable effects in repairing and regulating organisms (Progress in Modern Biomedicine 2008 Vol. 8 Num. 12 P2285 and Progress in Modern Biomedicine 2012 Vol. 12 Num. 6 P1187). At present, it has not been found out that the medium-intensity (300 gausses-5000 gausses) magnetic field has any side effects on human body. As a non-contact and non-medication physical effect therapy, the biological effect of magnetic fields has shown outstanding curative effects in cancer treatment, diabetes treatment, soft tissue pain treatment and psychotherapy, etc., and has been paid attention and recognized by medical staff and patients in recent years.

On the one hand, it has been found in the current research that when a static magnetic field (steady magnetic field) with a certain intensity continuously acts on organisms, oral pain caused by some diseases is able to be alleviated in a short time. In addition to alleviating pain, magnetic field has significant positive biological effects on blood flow and bones. On the other hand, biological effect products capable of static magnetic field therapy usually take a certain time to take effect, which makes it necessary to prepare and process magnetic materials into various products that are able to contact with human body for a long time, so as to provide an effective biological effect.

The biological effect products with static magnetic field have long been developed into various daily necessities including wearable devices, as well as magnetotherapeutic products such as mattresses, insoles and underwear or physiotherapy products with multiple functions with magnetotherapeutic effects at least. However, the components used to provide magnetic energy in these products all take hard permanent magnetic materials sintered into metals or ceramics as the core components, which causes these hard magnetic materials to seriously affect the comfort of human body when they are in use. Moreover, generally speaking, the hard sintered magnet is a single small-sized fixed shape in the manufacturing process. When the hard sintered magnet is used in wearable devices or as some functional inlays, these inlays and the surrounding non-magnetic areas will bring about obvious feeling differences, which will further affect the use experience. If a thick buffering layer is used, it will be unsightly and affect the magnetic effect, but if there is no buffering layer, it will make the users of the product extremely uncomfortable. Some existing technologies adopt the method of wrapping the hard magnet with plastic layer (such asCN201226797), but this method has not significantly resolved the above problems, and is far from meeting the requirements of magnetic biological effect components for portability, aesthetics, and comfort.

In addition, in terms of magnet material, the so-called "flexible magnet" prepared by bonding process has appeared in recent years, and is expected to be used as a magnetic material in biomedical field. At present, the main binders used in preparing flexible magnets are mainly rubber, and the manufacturing methods are mainly calendering. The existing methods of anisotropic flexible bonded magnets all need a thermoplastic binder represented by rubber, so the preparation process has to go through complicated processes, such as auxiliary preparation, inert powder mixing, formula coating, low-temperature mixing of materials, solvent volatilization, screw mixing or kneading with temperature, calendering with temperature, extrusion, etc. At the same time, the orientation technology in the calendering or extrusion process needs a very complicated and high-intensity external field solution.

The patent with publication number of CN1173028 introduces that anisotropic magnetic powder and thermosetting resin are mixed into a blank, and then the thermosetting resin in the blank is heated to a molten state, and the directional edge of the blank is compressed into a rigid anisotropic bonded magnet with a specified shape under the action of a directional magnetic field. Although thermosetting resin different from rubber is used in this method, in the manufacturing process, this technology needs to go through two temperature control processes: resin melting and resin curing. Because of the complexity of equipment conditions in the entire manufacturing process, the one-time preparation ability of large-format magnets is limited, and it is only suitable for producing small magnet parts. Crucially, although the material of this magnet is not metal, its texture is still hard, not flexible, and it is not applicable in the biomedical field.

SUMMARY

The purpose of the application is to provide a flexible permanent magnetic material, a preparation method and an application thereof in magnetic biological effect products, so as to solve the problems existing in the prior art, ensure that the magnetic material is soft, light and bendable, and at the same time, to make it have biomedical-grade magnetic field intensity.

In order to achieve the above objectives, the present application provides the following scheme.

The application provides a flexible permanent magnetic material, including the following components in parts by weight as raw materials:

0-70 parts of anisotropic neodymium iron boron powder, 0-40 parts of anisotropic samarium iron nitrogen powder and 3-20 parts of binder.

The anisotropic neodymium iron boron powder and the anisotropic samarium iron nitrogen powder are not 0 part by weight at the same time.

Optionally, the binder is thermosetting silica gel.

Optionally, the thermosetting silica gel is a two-component food-grade silica gel (AB silica gel).

Optionally, the raw materials of the flexible permanent magnetic material also include additives, such as clay powder, zinc stearate, dispersant, lubricant, etc. The material with two-dimensional layered structure contributes to the dispersion of magnetic powder and the sliding between particles, and plays the role of solid lubricant.

The lubricant may be molybdenum disulfide, conductive carbon powder or graphene, etc. The maximum amount of molybdenum disulfide is 5% of the total mass of magnetic powder, and the maximum amount of conductive carbon powder or graphene is 1% of the total mass of magnetic powder.

The application also provides a preparation method of the flexible permanent magnetic material, which includes the following steps:

step (1), after the raw materials are mixed according to parts by weight to obtain a mixture, defoaming treatment is carried out to remove gas in the mixture.

Step (2), pouring treatment is carried out on the mixture obtained in the step (1) at 15-35° C. to obtain hybrid magnet blank slurry. The pouring treatment time is 5-10 minutes.

Because of the high fluidity and controllable curing of silica gel, raw materials are able to be mixed well by conventional defoaming and stirring processes in the preparation process, which greatly simplifies the mixing process. Then, when the mixture is in a viscous liquid state, it is poured by a double-roller or three-roller grinder, and when the viscous liquid mixture is rolled, the pre-curing kneading of silica gel is completed.

And step (3) the hybrid magnet blank slurry is poured into a mold, the mold is heated while a magnetic field is applied to the upper and lower surfaces of the mold, the magnetic field is removed, and demoulding is carried out to obtain the flexible permanent magnetic material.

The above is the whole preparation process of the flexible bio-magnetic field material. According to the needs of the actual scene, the whole preparation process may be simplified as the following steps: material mixing-pre-curing kneading-pressure-free pouring-thermal insulation orientation-demoulding. The material obtained after demoulding may directly contact the human body without chemical stimulation. By reducing the contact distance with the human body, the surface magnetic energy acting on the human body may be further improved. The flexible bio-magnetic field material may be used in the field of static magnetic field biological effect treatment of mattresses, insoles, underwear, hats or different acupoints of the body, and is a human-friendly product with strong magnetic properties and flexible characteristics.

Optionally, the magnetic field intensity does not exceed 5000 gausses.

Optionally, the system temperature after heating in step (3) is 80-150° C., preferably 110-120° C.; the heating time is 1-8 h.

Optionally, the mold is made of a non-magnetic conductive material, such as copper or aluminum alloy.

The application further provides the application of the flexible permanent magnetic material in magnetic biological effect products.

Compared with the traditional magnets used in the medical care field, the flexible permanent magnetic material prepared by the application is lighter and easier to process and assemble, and whether used independently or assembled and spliced, the manufactured magnetic biological effect products have better human body affinity and efficient repair and adjustment effects on biological tissues.

According to the application, the anisotropic flexible permanent magnetic material is prepared by adopting moulding without the calendering technology.

The application discloses the following technical effects:

The application starts from the core material system for generating the static magnetic field, and silica gel is adopted as a strong magnetic material binder with flexible skin-friendly characteristics, and through the moulding process, the materials in the mold are capable of being simultaneously orientated without depending on the strong field under large-format condition, so as to obtain an anisotropic flexible magnet. Therefore, on the premise of ensuring a certain surface magnetic strength, the manufactured magnet is able to be molded into various required shapes in a moulding way, with adjustable size, soft and bendable materials. The manufactured magnet in the application is lighter than the traditional magnets used in the medical and health care field, and easier to process and assemble than the existing various bonded magnets regardless of independent usage or assembly and splicing. The manufactured magnetic biological effect products have better human affinity and are suitable for users to contact and wear for a long time or carry out auxiliary treatment.

BRIEF DESCRIPTION OF THE DRAWINGS

In order to explain the embodiments of the present application or the technical scheme in the prior art more clearly, the drawings needed in the embodiments will be briefly introduced below. Obviously, the drawings described below are only some embodiments of the present application, and other drawings may be obtained according to these drawings without creative work for ordinary people in the field.

DETAILED DESCRIPTION OF THE EMBODIMENTS

A number of exemplary embodiments of the present application will now be described in detail, and this detailed description should not be considered as a limitation of the present application, but should be understood as a more detailed description of certain aspects, characteristics and embodiments of the present application.

It should be understood that the terminology described in the present application is only for describing specific embodiments and is not used to limit the present application. In addition, for the numerical range in the present application, it should be understood that each intermediate value between the upper limit and the lower limit of the range is also specifically disclosed. The intermediate value within any stated value or stated range and every smaller range between any other stated value or intermediate value within the stated range are also included in the present application. The upper and lower limits of these smaller ranges may be independently included or excluded from the range.

Unless otherwise specified, all technical and scientific terms used herein have the same meaning as commonly understood by one of ordinary skill in the art to which this application relates. Although the present application only describes the preferred methods and materials, any methods and materials similar or equivalent to those described herein may also be used in the practice or testing of the present application. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present application without departing from the scope or spirit of the present application. Other embodiments will be apparent to the skilled person from the description of the application. The specification and example of this application are only exemplary.

The terms "comprising", "including", "having" and "containing" used in this article are all open terms, which means including but not limited to.

Figure 6:
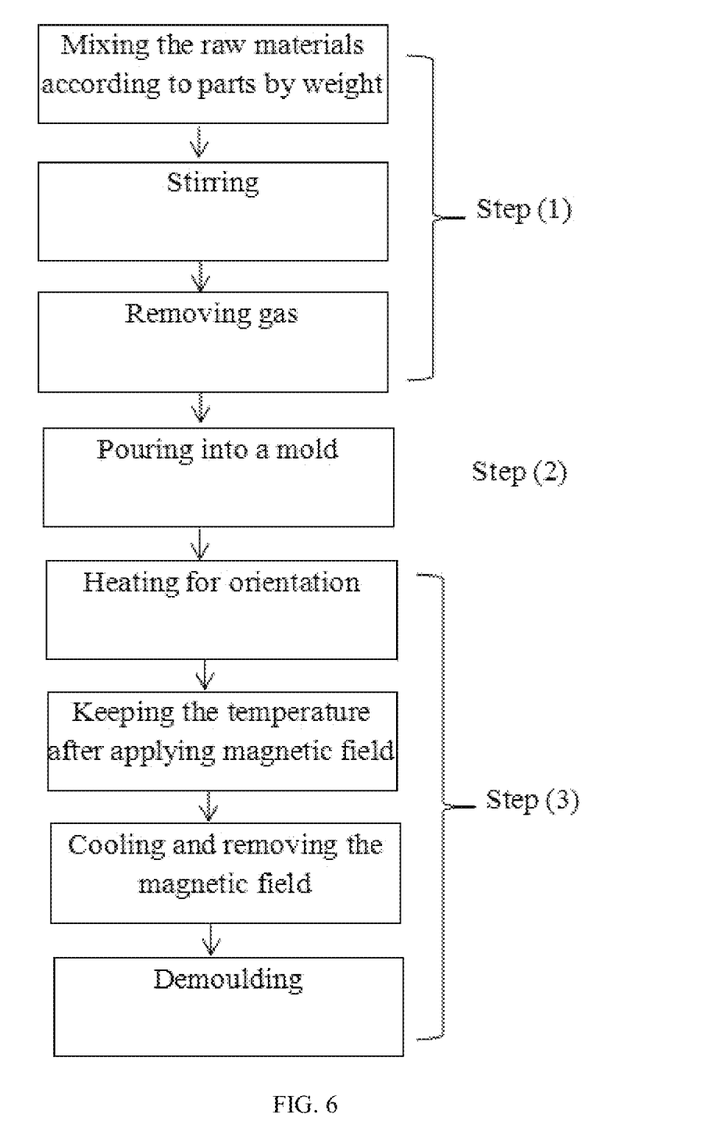
FIG. 6 is a process flow of a flexible permanent magnetic material.

As shown in FIG. 6, the process flow of a flexible permanent magnetic material is provided. The process flow of the flexible permanent magnetic material will be described with reference to flowing embodiments.

Embodiment 1

Preparation of a Silica Gel-Based Flexible Permanent Magnetic Material with High Magnetic Flux step (1), weighing 12.5 parts by weight of silica gel (food grade AB type), 65 parts by weight of anisotropic neodymium iron boron magnetic powder, 16 parts by weight of anisotropic samarium iron nitrogen magnetic powder, 0.5 part by weight of graphene, 3 parts by weight of titanium dioxide dispersant and 3 parts by weight of molybdenum disulfide;

step (2), mixing all the materials evenly in a mechanical stirrer, transferring the mixture to a vacuum gravity defoamer for processing for 5 minutes to remove the internal gas;

step (3), continuously transferring the obtained material to a three-roller grinder, and repeatedly pouring for 8 minutes, keeping the treatment temperature not higher than 40° C. in the whole process, so as to prevent the silica gel from curing, and obtaining the hybrid magnet blank slurry; and step (4), injecting the hybrid magnet blank slurry into an aluminum alloy mold, where the shape of the mold is a flat cuboid, the plane size of the mold may range from 15*15 square millimeters to 100*100 square millimeters, the thickness of the mold may range from 10 millimeters to 60 millimeters as required, and the mold is provided with air holes. After the hybrid magnet blank slurry is poured into the mold, the mold is gently pressed by the upper cover without pressurization. A magnetic field of 4200 gausses is applied in the thickness direction of the mold to orientate the internal hybrid magnet blank slurry. At the same time, the mold is heated to 120° C. and kept for 2 hours while the intensity of the orientation magnetic field is being maintained. After the time is over, the magnetic field is removed after cooling, and a flexible silica gel-based hybrid magnet is obtained, and the measured surface magnetism is 1300 gausses.

According to the format size of the actual application, a plurality of the above-mentioned silica gel-based hybrid magnets are repeatedly prepared. Because the material is orientated from north pole to south pole in the shape of thickness direction, the material may be closely spliced into a format environment of any size by alternating arrangement.

Figure 1:
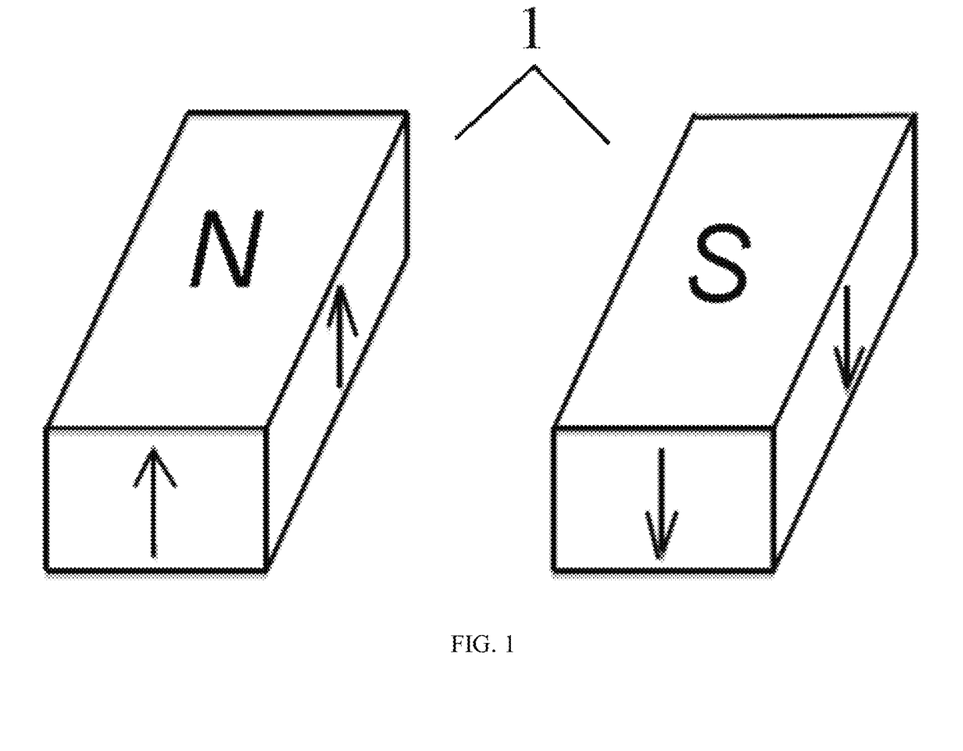
FIG. 1 is a schematic structural diagram of a cuboid flexible silica gel-based hybrid magnet in Embodiment 1.
Figure 2:
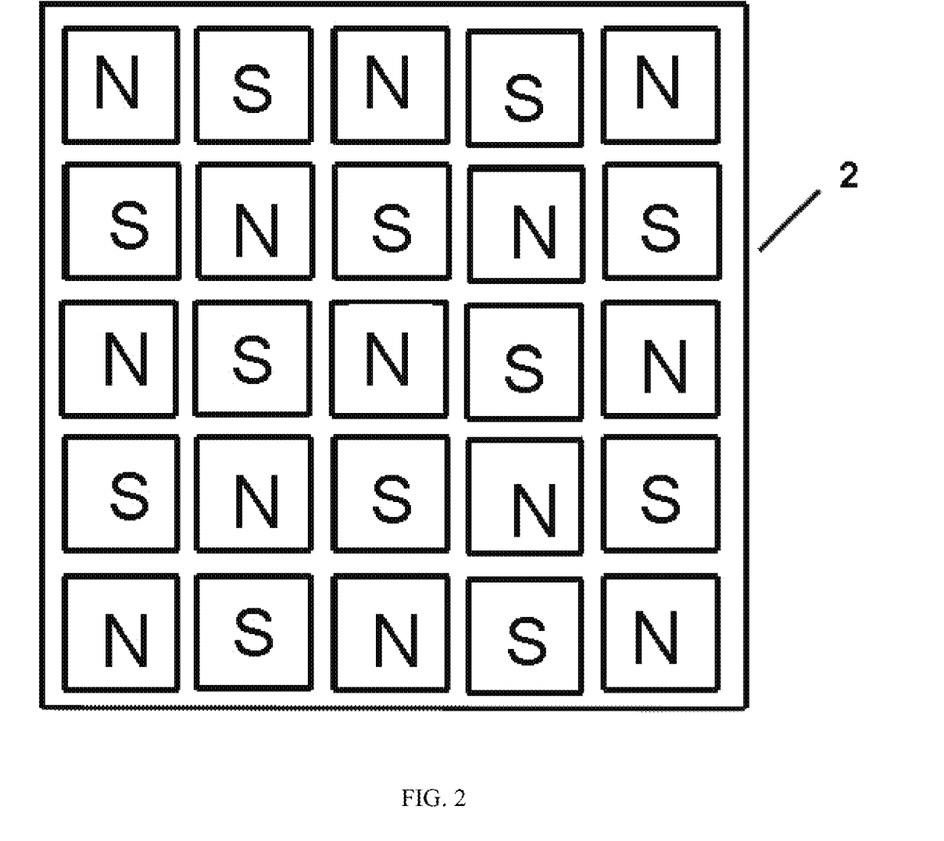
FIG. 2 is a schematic structural diagram of an integrated mattress spliced by a flexible silica gel-based hybrid magnet in embodiment 1.

Manufacture of Large-Format Integrated Mattress Based on Silica Gel-Based Hybrid Magnets For example, if the size of the mattress is 2000*2000 square millimeters, for a cuboid flexible silica gel-based hybrid magnet 1 (as shown in FIG. 1) with a size of 100*100 square millimeters, it is only necessary to lay 20 pieces in the xy direction. Because the north and south polar surfaces are alternately arranged from top to bottom, there will be no repulsion during installation and arrangement, but a certain adsorption force will be maintained between them, which is convenient for later assembly into an integrated mattress 2 (as shown in FIG. 2). After the silica gel mattress is assembled, its north and south polarity is perpendicular to the whole bed surface, and it basically becomes a magnetic field in the form of sinusoidal standing wave in vertical and horizontal directions. Because of soft material, the mattress is suitable for contacting directly with human skin, and the surface layer of the mattress may no longer be covered with any protective layer, or the surface layer of the mattress may only be simply decorated with cloth, cotton, linen, bamboo and other materials, so the contact distance with human body is very small, and provided magnetic field under the same comfort level is significantly higher than that of hard material mattresses.

Embodiment 2

Preparation of a Silica Gel-Based Flexible Permanent Magnetic Material with High Magnetic Flux step (1), weighing 14 parts by weight of silica gel (food grade AB type), 64 parts by weight of anisotropic neodymium iron boron magnetic powder, 15 parts by weight of anisotropic samarium iron nitrogen magnetic powder, 1 part by weight of graphene, 3.5 parts by weight of titanium dioxide dispersant and 2.5 parts by weight of molybdenum disulfide;

step (2), mixing all the materials evenly in a mechanical stirrer, transferring the mixture to a vacuum gravity defoamer for processing for 4 minutes to remove the internal gas;

step (3), continuously transferring the obtained material to a three-roller grinder, and repeatedly pouring for 5 minutes, keeping the treatment temperature not higher than 40° C. in the whole process, so as to prevent the silica gel from curing, and obtaining the hybrid magnet blank slurry; and step (4), pouring the hybrid magnet blank slurry into an aluminum alloy mold, where the size of the mold may be designed into special shapes with thin thickness as required, and the mold is provided with air holes. After the hybrid magnet blank slurry is poured into the mold, the mold is gently pressed by the upper cover without pressurization. A magnetic field of 3600 gausses is applied in the thickness direction of the mold to orientate the internal hybrid magnet blank slurry. At the same time, the mold is heated to 110° C. and kept for 30 minutes while the intensity of the orientation magnetic field is being maintained. After the time is over, the magnetic field is removed after cooling, and a flexible silica gel-based hybrid magnet is obtained, and the measured surface magnetism is 1025 gausses.

Figure 3:
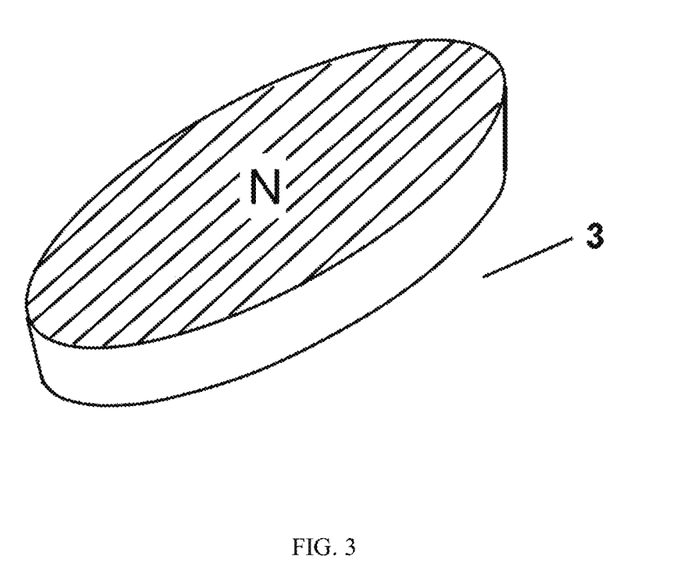
FIG. 3 is a schematic structural diagram of an acupoint patch in embodiment 2.

The prepared silica gel-based hybrid magnet is used as a human acupoint patch, a clothing inlay, or even a wearable object itself. For example, based on a mold with a diameter of 20 millimeters and a thickness of 3 millimeters, an acupoint patch 3 is prepared (as shown in FIG. 3). For another example, mold is designed in the shape of an insole. After the mold is cooled by the magnetic field insulation orientation technology, the insole has the distribution of magnetic field lines perpendicular to the direction of human sole, which is suitable for the magnetic stimulation scheme of foot acupuncture points or the whole sole.

Figure 4A:
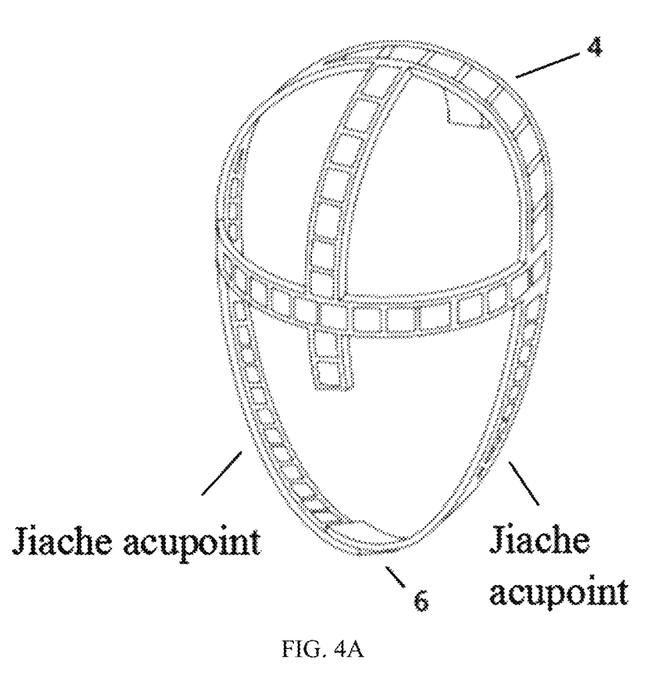
FIG. 4A is a front perspective view of a combined transcranial magnetic stimulation headband in embodiment 2.
Figure 4B:
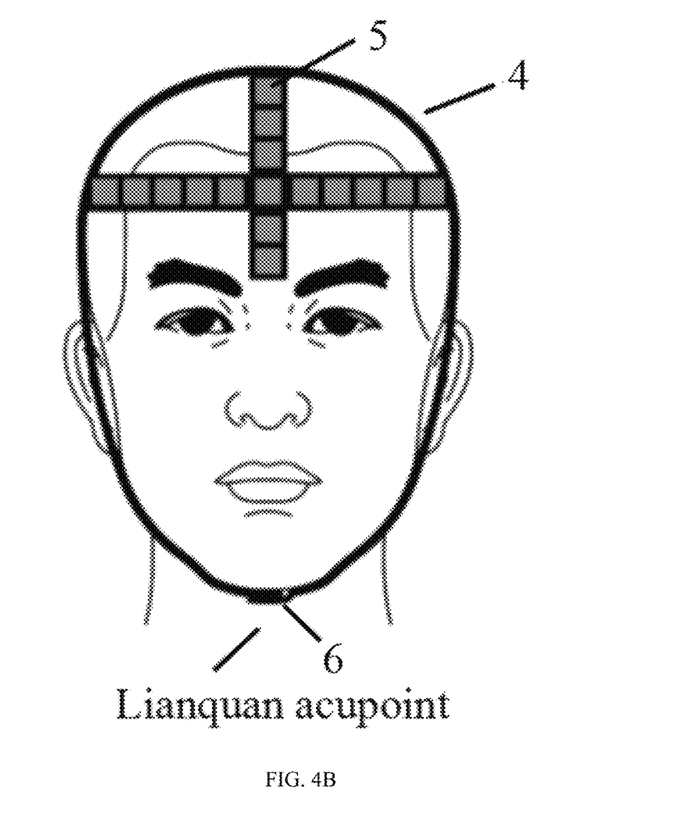
FIG. 4B is a front face wearing view of human body with a combined transcranial magnetic stimulation headband in embodiment 2.
Figure 4C:
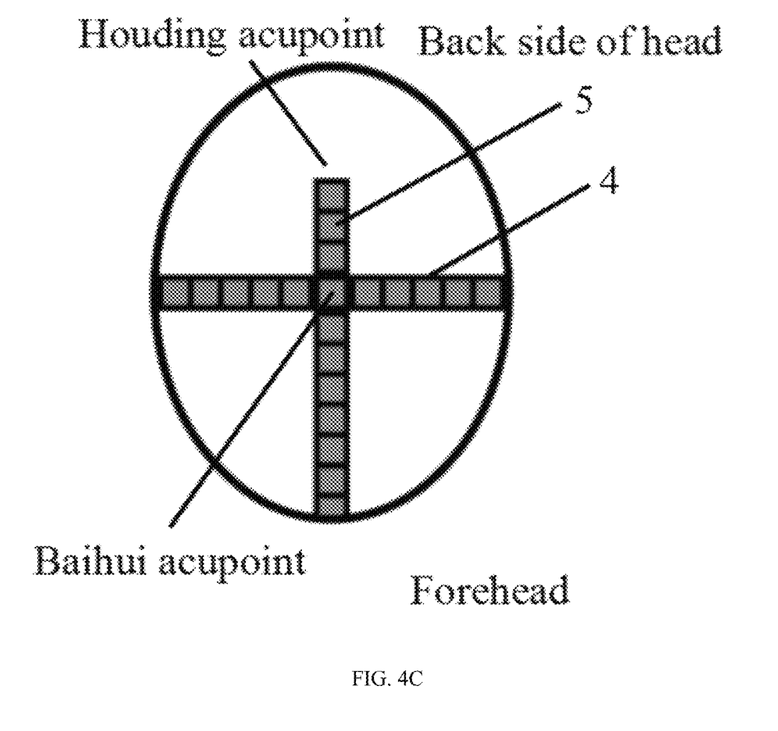
FIG. 4C is a top view of human body with a combined transcranial magnetic stimulation headband in embodiment 2.

Manufacture of Flexible Wearable Product Combined Transcranial Magnetic Stimulation Headband (as Shown in FIG. 4A, FIG. 4B, and FIG. 4C) Based on Silica Gel-Based Hybrid Magnet The headband takes the nonmagnetic connecting zone 4 as the main body, and the flexible silica gel-based hybrid magnet 5 with north and south polar being tiny curved surface is embedded in the main body. The distribution on the human head is roughly as shown in FIG. 4A, FIG. 4B, and FIG. 4C, and the end 6 of the connecting zone may be butted by magnetic buckle or adhesive buckle. The headband has the advantages of portability, strong magnetism, free selection of magnetic stimulation points, etc. It may be directly applied to the head and face of human body, and may be worn for a short time or for a long time during sleep, which is helpful to improve insomnia and other mental and emotional problems caused by abnormal discharge of brain cells.

Embodiment 3

Preparation of a Silica Gel-Based Flexible Permanent Magnetic Material with High Magnetic Flux step (1), weighing 25 parts by weight of silica gel (food grade AB type), 50 parts by weight of anisotropic neodymium iron boron magnetic powder, 22 parts by weight of anisotropic samarium iron nitrogen magnetic powder, and 3 parts by weight of zinc stearate;

step (2), mixing all the materials evenly in a mechanical stirrer, transferring the mixture to a vacuum gravity defoamer for processing for 5 minutes to remove the internal gas, and obtaining the hybrid magnet blank slurry without pouring treatment; and step (3), injecting the hybrid magnet blank slurry into an aluminum alloy mold, where the shape of the mold is a flat cuboid, the plane size of the mold may range from 15*15 square millimeters to 100*100 square millimeters, the thickness of the mold may range from 10 millimeters to 60 millimeters as required, and the mold is provided with air holes. After the hybrid magnet blank slurry is poured into the mold, the mold is gently pressed by the upper cover without pressurization. A magnetic field of 4250 gausses is applied in the thickness direction of the mold to orientate the internal hybrid magnet blank slurry. At the same time, the mold is heated to 120° C. and kept for 1 hour while the intensity of the orientation magnetic field is being maintained. After the time is over, the magnetic field is removed after cooling, and a flexible silica gel-based hybrid magnet is obtained, and the measured surface magnetism is 835 gausses.

The prepared silica gel-based hybrid magnet may be used to manufacture an integrated mattress according to a way as in embodiment 1.

In the case of a large proportion of silica gel, this embodiment omits the step of pouring and rolling, and the surface magnetism of the final product is slightly lower.

Embodiment 4

Preparation of a Silica Gel-Based Flexible Permanent Magnetic Material with High Magnetic Flux step (1), weighing 15 parts by weight of silica gel (food grade AB type), and 85 parts by weight of anisotropic neodymium iron boron magnetic powder;

step (2), mixing all the materials evenly in a mechanical stirrer, transferring the mixture to a vacuum gravity defoamer for processing for 5 minutes to remove the internal gas;

step (3), continuously transferring the obtained material to a three-roller grinder, and repeatedly pouring for 10 minutes, keeping the treatment temperature not higher than 40° C. in the whole process, so as to prevent the silica gel from curing, and obtaining the hybrid magnet blank slurry; and step (4), injecting the hybrid magnet blank slurry into an aluminum alloy mold, where the shape of the mold is a flat cuboid, the plane size of the mold may range from 15*15 square millimeters to 100*100 square millimeters, the thickness of the mold may range from 10 millimeters to 60 millimeters as required, and the mold is provided with air holes. After the hybrid magnet blank slurry is poured into the mold, the mold is gently pressed by the upper cover without pressurization. A magnetic field of 4200 gausses is applied in the thickness direction of the mold to orientate the internal hybrid magnet blank slurry. At the same time, the mold is heated to 120° C. and kept for 1 hour while the intensity of the orientation magnetic field is being maintained. After the time is over, the magnetic field is removed after cooling, and a flexible silica gel-based hybrid magnet is obtained, and the measured surface magnetism is 1200 gausses.

The prepared silica gel-based hybrid magnet may be used to manufacture an integrated mattress according to a way as in embodiment 1.

Embodiment 5

Preparation of a Silica Gel-Based Flexible Permanent Magnetic Material with High Magnetic Flux step (1), weighing 25 parts by weight of silica gel (food grade AB type), and 75 parts by weight of anisotropic samarium iron nitrogen powder;

step (2), mixing all the materials evenly in a mechanical stirrer, transferring the mixture to a vacuum gravity defoamer for processing for 5 minutes to remove the internal gas;

step (3), continuously transferring the obtained material to a three-roller grinder, and repeatedly pouring for 8 minutes, keeping the treatment temperature not higher than 40° C. in the whole process, so as to prevent the silica gel from curing, and obtaining the hybrid magnet blank slurry; and step (4), injecting the hybrid magnet blank slurry into an aluminum alloy mold, where the shape of the mold is a flat cuboid, the plane size of the mold may range from 15*15 square millimeters to 100*100 square millimeters, the thickness of the mold may range from 10 millimeters to 60 millimeters as required, and the mold is provided with air holes. After the hybrid magnet blank slurry is poured into the mold, the mold is gently pressed by the upper cover without pressurization. A magnetic field of 4200 gausses is applied in the thickness direction of the mold to orientate the internal hybrid magnet blank slurry. At the same time, the mold is heated to 110° C. and kept for 1 hour while the intensity of the orientation magnetic field is being maintained. After the time is over, the magnetic field is removed after cooling, and a flexible silica gel-based hybrid magnet is obtained, and the measured surface magnetism is 980 gausses.

The prepared silica gel-based hybrid magnet can be used to manufacture an integrated mattress according to a way as in embodiment 1.

Comparative Example 1

The only difference from embodiment 1 is that no orientation magnetic field is applied.

The surface magnetic intensity of the prepared silica gel-based hybrid magnet is 266 gausses.

Comparative Example 2

The only difference from embodiment 1 is that in step (4), the mold is heated to 65° C. and kept for 4 hours and 15 minutes.

After the time is over, the magnetic field is removed after cooling, and the appearance of the material is examined. A complete silica gel-based hybrid magnet not obtained, and some silica gel is not cured, so the material is cracked and deformed under the action of the internal magnetic field, which is caused by the low curing temperature.

Figure 5:
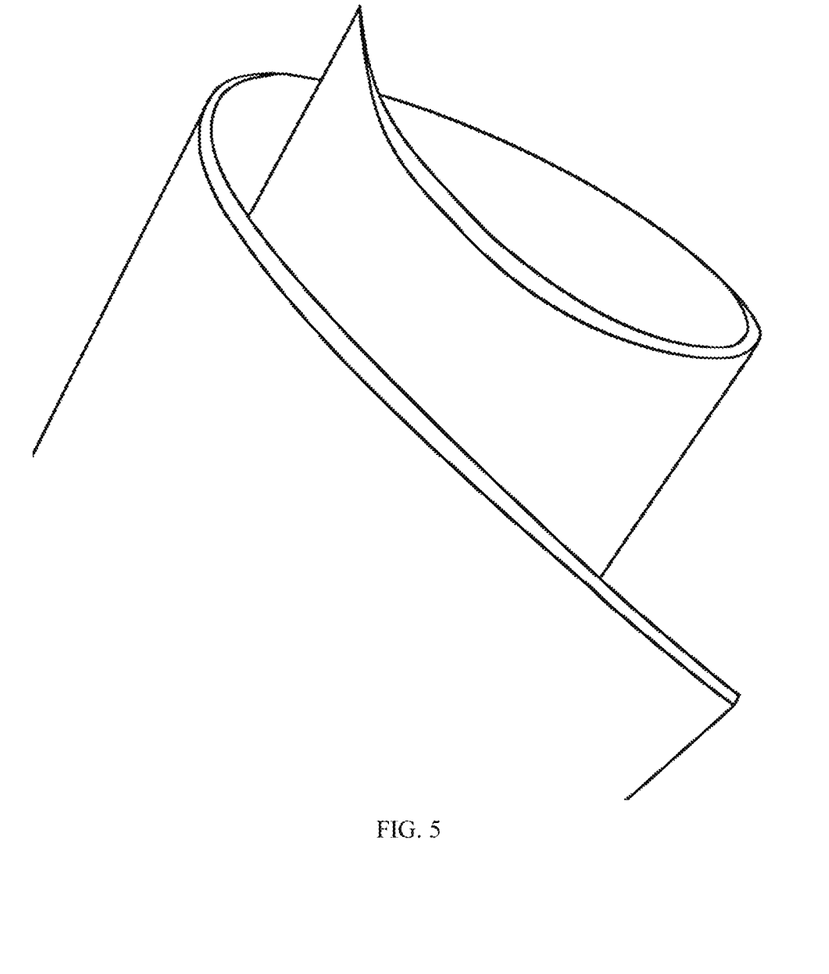
FIG. 5 is a physical diagram of a cuboid flexible silica gel-based hybrid magnet in embodiment 1.

FIG. 5 is a physical diagram of the cuboid flexible silica gel-based hybrid magnet (embodiment 1) prepared by the present application, and it can be seen that it has good flexibility.

The above-mentioned embodiments only describe the preferred mode of the application, and do not limit the scope of the application. Under the premise of not departing from the design spirit of the application, various modifications and improvements made by ordinary technicians in the field to the technical scheme of the application shall fall within the protection scope determined by the claims of the application.

What is claimed is:
1. A method for preparing a flexible permanent magnetic material, comprising:
   (1) mixing raw materials according to parts by weight, followed by carrying out defoaming treatment to remove gas in a mixture;
   wherein the raw materials comprise: 0-70 parts by weight of anisotropic neodymium iron boron powder, 0-40 parts by weight of anisotropic samarium iron nitrogen powder, 3-20 parts by weight of a binder, clay powder, zinc stearate, a dispersant and a lubricant;
   wherein the anisotropic neodymium iron boron powder and the anisotropic samarium iron nitrogen powder are not 0 at a same time;
   wherein the binder is two-component food-grade silica gel; and
   wherein the lubricant is conductive carbon powder or graphene with a maximum amount that is 1% of a total mass of the anisotropic neodymium iron boron powder and the anisotropic samarium iron nitrogen powder;
   (2) carrying out pouring treatment at 15-35° C. on the mixture obtained in the step (1) to obtain hybrid magnet blank slurry; and
   (3) pouring the hybrid magnet blank slurry into a mold, heating while applying a magnetic field to upper and lower surfaces of the mold, then removing the magnetic field, and demoulding to obtain the flexible permanent magnetic material; wherein a magnetic field intensity does not exceed 5000 gausses;
   wherein after the heating in the step (3), a system temperature is 80-150° C., and a heating duration is 1-8 h; and the mold is made of a non-magnetic conductive material.

2. The method for preparing the flexible permanent magnetic material according to claim 1, wherein the mold is made of copper or aluminum alloy.

3. The method for preparing the flexible permanent magnetic material according to claim 1, wherein after the heating in the step (3), the system temperature is 110-120° C.

* * * * *